United States Patent
Ericsson

(10) Patent No.: US 6,270,756 B1
(45) Date of Patent: Aug. 7, 2001

(54) WEIGHT LOSS INDUCED BY ALPHA INTERFERON AND GAMMA INTERFERON

(75) Inventor: Arthur Dale Ericsson, Houston, TX (US)

(73) Assignee: RX/IBR Corporation, Houston, TX (US)

( * ) Notice: Subject to any disclaimer, the term of this patent is extended or adjusted under 35 U.S.C. 154(b) by 0 days.

(21) Appl. No.: 09/385,989

(22) Filed: Aug. 30, 1999

(51) Int. Cl.[7] .......................... A61K 38/21; A61K 35/12; A61K 35/32; A61K 35/36; A61K 35/26

(52) U.S. Cl. .................. 424/84.5; 424/85.5; 424/573; 424/574; 424/578; 514/909

(58) Field of Search .................................... 424/85.4, 573, 424/574, 578; 514/909

(56) References Cited

PUBLICATIONS

Flores et al., J Clin Invest., vol. 83: 1614–1622. Infusion of tumor necrosis factor/cachectin promotes muscle catabolism in the rat: a synergistic effect with interleukin 1, 1989.*

Byrsk et al., Anticancer Research, vol. 17: 3387–3392. Modulation by interferon–gamma of zinc–alpha2–glycoprotein gene expression in human epithelial cell lines, 1997.*

Todorov et al., Cancer Research, vol. 58: 2353–2358. Purification and characterization of a tumor lipid–mobilizing factor, Jun. 1, 1998.*

* cited by examiner

Primary Examiner—Christopher R. Tate
Assistant Examiner—Michele Flood
(74) Attorney, Agent, or Firm—John R Casperson

(57) ABSTRACT

The invention is based on the discovery that substances which release ZAG proteins from lymphocytes also cause accelerated weight loss in humans. By administering an amount of the substance which is effective to cause the weight loss but is beneath an amount which causes side effects, a very desirable "dieter's aid" is provided. A dilute mixture of alfa interferon and gamma interferon in an aqueous medium is highly suitable for this purpose. It is administered at a much lower dosage than is generally employed for antibiotic purposes, thereby avoiding generally universal side effects. For periods of time extending at least for a few days, the weight loss composition of the invention causes weight loss at a greater weight than would be expected from fasting, at least for seriously overweight individuals.

13 Claims, No Drawings

WEIGHT LOSS INDUCED BY ALPHA INTERFERON AND GAMMA INTERFERON

BACKGROUND OF THE INVENTION

Body weight and obesity are like the weather: Everyone talks about it, but no one seems able to do much about it. In recent years researchers have learned a great deal about the cause and ramifications of obesity. Metabolism-the way we absorb, utilize, break down and eliminate the waste from food stuffs-is only a part of the difference between individuals. In order to understand these differences, the playing field must be analyzed, not a macro-cellular level, but rather at a micro-cellular level.

At the micro-cellular level, uncoupling proteins (UCPs) have been found to exist and they dissociate the reactions that break down food from those that produce the body's chemical energy. These UCPs let hydrogen ions pass through the cellular inner mitochondrial membrane, thereby abolishing the hydrogen ion gradient needed to drive ATP synthesis. If the UCPs activity could be increased by 1–2% then there would be an increase fat oxidation and thermogenesis. This would translate into a boost in resting metabolic rates and subsequent weight loss for millions of individuals. A technique to increase the action of the body's own uncoupling proteins would be very desirable, and could add years of life for certain individuals.

SUMMARY OF THE INVENTION

In one embodiment of the invention, there is provided a method for promoting weight loss in humans. The method is carried out by administering effective amount of a substance which actuates the production and release of ZAG proteins from lymphocytes, but preferably beneath an amount which causes side effects.

In another embodiment of the invention, there is provided a composition of matter highly suitable for use in the above method. The composition comprises a dilute mixture of alfa interferon and gamma interferon in an aqueous medium. The concentration and daily dosage of the interferons is generally well beneath concentrations and dosages employed for antibiotic purposes.

In still another embodiment of the invention, there is provided a method for causing weight loss in humans which is more effective than fasting. The method is carried out by administering an effective amount of a weight-loss composition comprising both alfa interferon and gamma interferon on a daily basis for a period of time in the range of 3 days to 30 days. At least during the initial part of the period, weight loss for many individuals occurs at a greater rate than would be caused by fasting.

In still another embodiment of the invention, there is provided a method for a human to self-induce weight loss. The method is carried out by self-administering an effective amount of a weight-loss composition in a manner and amount as described above.

DETAILED DESCRIPTION OF THE INVENTION

We have found that a substance which triggers the production and release of ZAG proteins from lymphocytes will cause weight loss when administered to humans. The amount of the substance employed should be beneath any amount which causes side effects.

The substance is preferably administered as a weight-loss composition which comprises a mixture of alfa interferon and gamma interferon. On a daily basis, the amount employed is much lower than an amount which would constitute an effective anti-biotic.

Surprising, the weight-loss composition causes a loss of weight at a rate faster than fasting for many people, at least during the initial part of the treatment period. In other words, many people exhibit weight loss at a rate of greater than 0.5 pounds per day. The rate of weight loss is achieved without dieting. In other words, program participants may ingest normal amounts of food, for example, in the range of 1,500 to 2,500 calories per day.

A daily dose of the weight-loss composition of the invention can be effectively self-administered, and is preferably nasally or buccally self-administered over a plurality of applications. More preferably, the daily dosage is administered sublingually as a spray, tablet, capsule or lozenge. Administering the daily dosage sublingually as a spray has been tested with good results and is therefore most preferred.

A daily dosage in the range of 50 to 5,000 units of alfa interferon and 50 to 5,000 units of gamma interferon is believed generally suitable in accordance with the invention, and should not be so high as to produce side effects. In contrast, an amount of interferon which is effective as an antibiotic is generally at least 1,000,000 units daily, and almost always produces undesirable side effects.

For spray application, the weight loss composition most preferably comprises a dilute mixture of alfa interferon and gamma interferon in an aqueous medium. Phosphate buffer solution is a highly suitable aqueous medium. A concentration of alfa interferon at a concentration in the range of 150,000–15,000,000 IU/liter and gamma interferon at a concentration in the range of 150,000–15,000,000 IU/liter is believed generally suitable. A concentration of alfa interferon in the range of 500,000–5,000,000 IU/liter and gamma interferon at a concentration in the range of 500,000–5,000,000 IU/liter is preferred.

The weight loss composition of the invention can be conveniently supplied and distributed in containers containing a few milliliters of the inventive composition in liquid form. Preferably, the containers constitute spray bottles which are configured for administering a metered dose of about 0.1 ml per spray. Such a bottle will apply about 150 units of alfa interferon and about 150 units of gamma interferon per dose when it contains alfa and gamma interferon at a concentration of about 1,500,00 IU/liter each. This dosage, applied three times per day, has been tested with good results.

During testing, it was noted that the rate of weight loss was generally higher during the initial part of the test period than during the latter part. It is thus believe that the weight-loss composition will be most effective when administered for relatively short periods of time. Generally speaking, it is thought that the daily dosage of the weight loss composition should be divided and administered as a plurality of doses for a treatment period which is in the range of from about 3 days to about 30 days and then discontinued for a similar period of time. If additional weight loss is desirable, then administration of the weight-loss composition can be recommenced. The weight loss composition can be alternately administered or withheld for similar periods of time until a predetermined amount of weight loss has occurred.

EXEMPLARY EMBODIMENT

Obesity and severe weight loss are not polar ends of a linear process. They both are, in fact, the end result of a complex series of interactions that culminate in a net change in body weight. Most of the current strategies for treatment of obesity target the obesity signaling pathway by inhibiting serotonergic neurons, inhibiting noradrenergic neurons, interfering with obesity receptors, stimulating endocrine function and/or acting on pancreatic lipases.

Cachexia (or severe weight loss), in stark contrast to obesity, is a wasting syndrome caused by depletion of occasionally muscle and always adipose tissue that is ultimately present in the majority of patients with cancer, AIDS and other life threatening diseases. A soluble glycoprotein present in the serum and other bodily fluids appears responsible for the fat-depletion component of cachexia, since it stimulates lipid breakdown in adipocytes and reduces fat stores. Moreover, this protein is overexpressed in carcinomas that induce fat loss but not in other tumors. This glycoprotein is called the ZAG protein from its tendency to precipitate with zinc salts and its electrophoretic mobility in the region of alfa-2 globulins. It appears that ZAG normally functions to regulate lipid degradation, which increases to a pathological extent in cachexia.

We have found a new natural formulation, which we have named ObeX, that appeared to activate the production and release of ZAG proteins from lymphocytes. This activates the lymphocyte's release of the ZAG protein mechanism to result in adipocyte shrinkage and cell loss and thus promotes weight loss.

The formulation used in the clinical trial described below was made by dissolving 3 million units of alfa interferon and 3 million units of gamma interferon in 2 liters of sterile phosphate buffer solution. The phosphate buffer was as described in U.S. Pat. No. 5,773,241. The formulation was dispensed in 30 ml spray bottles to our test subjects. The formulation, labeled ObeX, was sprayed into the oral cavity, specifically 0.1 ml under the tongue, three times a day, for ten days. Each dose delivered about 150 units of alfa interferon and 150 of gamma interferon.

The following table illustrates the individual and mean responses of this study group.

TABLE I

ObeX Study

| Subject | Wt. 0 | Wt. 1 | Wt. 2 | Wt. 3 | Wt. 4 | Wt. 5 | Wt. 6 | Wt. 7 |
|---|---|---|---|---|---|---|---|---|
| 1 | 183 | 181 | 181 | 182 | 180 | 180 | 180 | 179 |
| 2 | 155 | | | | | | | 154 |
| 3 | 300 | | | | | | | 296 |
| 4 | 143 | | | | | | | 136 |
| 5 | 338 | | 330 | | 327 | | 321 | 319 |
| 6 | 245 | | 238 | | 240 | | 238 | 238 |
| 7 | 143 | | | | | | | 135 |
| 8 | 230 | 227 | 223 | 223 | 223 | 223 | 222 | 222 |
| 9 | 242 | 239 | | 237 | | 235 | | 235 |
| 10 | 226 | | | | | | | 223 |
| 11 | 176 | | | | | | | 173 |
| 12 | 298 | | | | | | | 280 |
| 13 | 128 | | | | | | | 128 |
| 14 | 236 | | | 217 | | | | 210 |
| 15 | 222 | | | | | | | 220 |
| 16 | 205 | | | | | | | 200 |
| 17 | 197 | | | | | | | 182 |
| Total | 3667 | | | | | | | 3530 |
| Mean Wt | 215.7 | | | | | | | 207.4 |

Discussion

The test subjects were 17 normal obese adults with whose initial weight ranged from 128 to 338 pounds with a mean of 215.7 pounds. Each subject was instructed not to diet and to live a normal life and in addition to use ObeX spray three times per day and report weight/girth frequently. One-two weeks later the weight ranged from 128 to 319 pounds, with a mean of 207.4 pounds. There were no reported side effects and the overall mean weight loss for this group of subjects was 8.3 pounds. Moreover, from 1–5 inches was lost in the girth as measured at the waist for this group of subjects. It appears that from the data that the more morbidly obese patients lost more weight from ObeX than subjects that were only mildly obese, and that most of the weight loss was in the initial portion of the study. Amazingly, the rate of weight loss over the course of the study was 0.83 pounds per day, whereas total fasting (zero caloric intake) would be expected to result in a rate of weight loss of only 0.5 pounds per day in persons of normal metabolisms.

While certain preferred embodiments of the invention have been described herein, the invention is not to be construed as being so limited, except to the extent that such limitations are found in the claims.

What is claimed is:

1. A method for promoting weight loss in a human in need thereof, said method comprising
   administering to said human an effective amount, which, of a mixture of alpha interferon and gamma interferon to cause the production and release of zinc-$\alpha_2$-glycoproteins from lymphocytes in said human, thereby stimulating lipid breakdown and a reduction of fat stores in said human, such zinc-α2-glycoproteins having a tendency to precipitate with zinc salts and exhibiting electrophoretic mobility in the region of alpha-2 globulins.

2. A method for promoting weight loss in a human in need thereof, said method comprising
   administering to said human an effective amount, of a mixture of alpha interferon and gamma interferon to cause the production and release of zinc-$\alpha_2$-glycoproteins from lymphocytes in said human, thereby stimulating lipid breakdown and a reduction of fat stores in said human, such zinc-$\alpha_2$-glycoproteins having a tendency to precipitate with zinc salts and exhibiting electrophoretic mobility in the region of alpha-2 globulins,
   wherein a daily dosage in the range of 50 to 5,000 units of alpha interferon and 50 to 5,000 units of gamma interferon is administered.

3. A method as in claim 2 wherein the daily dosage is nasally or buccally administered over a plurality of applications.

4. A method as in claim 2 wherein the daily dosage is administered sublingually as a spray, tablet, capsule or lozenge.

5. A method as in claim 2 wherein the daily dosage is administered sublingually as a spray having a volume of about 0.1 ml and containing about 150 units of alpha interferon and 150 units of gamma interferon applied three times daily.

6. A method as in claim 5 wherein the daily dosage is administered for a first period of time in the range of 3 days to about 30 days and then is withheld for a second period of time.

7. A method as in claim 6 wherein the second period of time is in the range of from about 3 days to about 30 days, and wherein said method further comprises continuing the administration of the daily dosage for a third period of time in the range of 3 days to about 30 days after the passage of the second period.

8. A method as in claim 2 further comprising alternately administering the daily dosage for a first period of time and withholding the daily dosage for a second period of time until a predetermined amount of weight loss has occurred.

9. A method for causing weight loss in a human comprising administering to said human on a daily basis for a period of time in the range of 3 days to 30 days an effective amount of a weight-loss composition comprising both alpha interferon and gamma interferon to cause weight loss at a greater rate than fasting.

10. A method for causing weight loss in a human in need thereof comprising
   administering to said human on a daily basis for a period of time in the range of 3 days to 30 days an effective amount of a weight-loss composition comprising both alpha interferon and gamma interferon to cause weight loss at a greater rate than fasting
   wherein a daily dosage in the range of 50 to 5,000 units of alpha interferon and 50 to 5,000 units of gamma interferon is administered,
said process further comprising
   predetermining a desired amount of weight loss, and
   discontinuing the weight-loss composition when the desired amount of weight loss has been reached.

11. A method for a human to self-induce weight loss comprising self-administering an effective amount of a weight-loss composition comprising both alpha interferon and gamma interferon to cause weight loss at a greater rate than fasting for a period of time in the range of 3 days to 30 days.

12. A method for a human to self-induce weight loss comprising
   self-administering an effective amount of a weight-loss composition comprising both alpha interferon and gamma interferon to cause weight loss at a greater rate than fasting to 30 days,
   wherein a daily dosage of the weight-loss composition is nasally or buccally, administered over a plurality of applications and the daily dosage is in the range of 50 to 5,000 units of alpha interferon and 50 to 5,000 units of gamma interferon.

13. A method as in claim 12 wherein the daily dosage is administered sublingually as a spray having a volume of about 0.1 ml and containing about 150 units of alpha interferon and 150 units of gamma interferon applied three times daily.

* * * * *